United States Patent
West et al.

(10) Patent No.: US 9,763,641 B2
(45) Date of Patent: Sep. 19, 2017

(54) METHOD AND SYSTEM FOR IMAGING A VOLUME OF TISSUE WITH TISSUE BOUNDARY DETECTION

(71) Applicant: Delphinus Medical Technologies, Inc., Plymouth, MI (US)

(72) Inventors: Erik West, Rochester Hills, MI (US); Olivier Roy, Royal Oak, MI (US); Steven Schmidt, Clinton Township, MI (US)

(73) Assignee: Delphinus Medical Technologies, Inc., Novi, MI (US)

( * ) Notice: Subject to any disclaimer, the term of this patent is extended or adjusted under 35 U.S.C. 154(b) by 1024 days.

(21) Appl. No.: 14/015,459

(22) Filed: Aug. 30, 2013

(65) Prior Publication Data
US 2014/0066772 A1  Mar. 6, 2014

Related U.S. Application Data
(60) Provisional application No. 61/694,999, filed on Aug. 30, 2012.

(51) Int. Cl.
| | | |
|---|---|---|
| *A61B 8/00* | (2006.01) | |
| *A61B 8/08* | (2006.01) | |
| *A61B 8/15* | (2006.01) | |

(52) U.S. Cl.
CPC ............. *A61B 8/0825* (2013.01); *A61B 8/15* (2013.01); *A61B 8/4494* (2013.01); *A61B 8/406* (2013.01)

(58) Field of Classification Search
CPC ....... A61B 8/0825; A61B 8/4494; A61B 8/15; A61B 8/406

(Continued)

(56) References Cited

U.S. PATENT DOCUMENTS

| | | |
|---|---|---|
| 3,154,067 A | 10/1964 | Stenstrom et al. |
| 3,771,355 A | 11/1973 | Sachs |

(Continued)

FOREIGN PATENT DOCUMENTS

| | | |
|---|---|---|
| AU | 3443295 A | 5/1996 |
| CA | 2324602 A | 9/1999 |

(Continued)

OTHER PUBLICATIONS

Azhari et al., "Volumetric Imaging with Ultrasonic Spiral CT," Radiol 212 (1999) 270-275.

(Continued)

*Primary Examiner* — Sanjay Cattungal
(74) *Attorney, Agent, or Firm* — Wilson Sonsini Goodrich & Rosati

(57) ABSTRACT

A method and system for imaging a volume of tissue and defining a tissue boundary comprising: receiving a baseline dataset representative of a first set of signals interacting with a medium; receiving a reconstruction dataset representative of a second set of signals interacting with the medium and the volume of tissue present in the medium; determining a set of direct emitter-receiver pairs, each defining a direct trajectory that does not pass through the volume of tissue; from the set of direct emitter-receiver pairs, determining a set of tangential emitter-receiver pairs, each defining a bounding vector comprising a tangent point along the tissue boundary; determining a set of interior pixels, of the reconstruction dataset, characterized by a set of pixel locations within the tissue boundary; and reconstructing pixels of the set of interior pixels, thereby transforming the baseline and the reconstruction datasets into an image rendering of the volume of tissue.

16 Claims, 5 Drawing Sheets

(58) Field of Classification Search
USPC .................................................. 600/437–469
See application file for complete search history.

(56) References Cited

U.S. PATENT DOCUMENTS

| | | |
|---|---|---|
| 3,881,466 A | 5/1975 | Wilcox |
| 3,886,489 A | 5/1975 | Jones |
| 3,925,610 A | 12/1975 | French et al. |
| 4,028,934 A | 6/1977 | Sollish |
| 4,059,010 A | 11/1977 | Sachs |
| 4,075,883 A | 2/1978 | Glover |
| 4,105,018 A | 8/1978 | Greenleaf et al. |
| 4,144,877 A | 3/1979 | Frei et al. |
| 4,222,274 A | 9/1980 | Johnson |
| 4,250,894 A | 2/1981 | Frei et al. |
| 4,317,369 A | 3/1982 | Johnson |
| 4,328,707 A | 5/1982 | Clement et al. |
| 4,363,326 A | 12/1982 | Kopel |
| 4,412,288 A | 10/1983 | Herman |
| 4,431,008 A | 2/1984 | Wanner et al. |
| 4,433,690 A | 2/1984 | Green et al. |
| 4,481,948 A | 11/1984 | Sole |
| 4,509,368 A | 4/1985 | Whiting et al. |
| 4,515,165 A | 5/1985 | Carroll |
| 4,541,436 A | 9/1985 | Hassler et al. |
| 4,542,744 A | 9/1985 | Barnes et al. |
| 4,562,540 A | 12/1985 | Devaney |
| 4,564,019 A | 1/1986 | Miwa |
| 4,606,342 A | 8/1986 | Zamba et al. |
| 4,646,756 A | 3/1987 | Watmough et al. |
| 4,662,222 A | 5/1987 | Johnson |
| 4,671,256 A | 6/1987 | Lemelson |
| 4,733,562 A | 3/1988 | Saugeon |
| 4,855,911 A | 8/1989 | Lele et al. |
| 4,858,124 A | 8/1989 | Lizzi et al. |
| 4,917,096 A | 4/1990 | Englehart et al. |
| 4,932,414 A | 6/1990 | Coleman et al. |
| 4,941,474 A | 7/1990 | Pratt, Jr. |
| 5,003,979 A | 4/1991 | Merickel et al. |
| 5,025,792 A | 6/1991 | Hon et al. |
| 5,029,476 A | 7/1991 | Metala et al. |
| RE33,672 E | 8/1991 | Miwa |
| 5,095,909 A | 3/1992 | Nakayama et al. |
| 5,103,129 A | 4/1992 | Slayton et al. |
| 5,143,069 A | 9/1992 | Kwon et al. |
| 5,158,071 A | 10/1992 | Umemura et al. |
| 5,158,536 A | 10/1992 | Sekins et al. |
| 5,178,147 A | 1/1993 | Ophir et al. |
| 5,179,455 A | 1/1993 | Garlick |
| 5,212,571 A | 5/1993 | Garlick et al. |
| 5,255,683 A | 10/1993 | Monaghan |
| 5,260,871 A | 11/1993 | Goldberg |
| 5,267,566 A | 12/1993 | Choucair et al. |
| 5,268,876 A | 12/1993 | Rachlin |
| 5,269,309 A | 12/1993 | Fort et al. |
| 5,280,788 A | 1/1994 | Janes et al. |
| 5,296,910 A | 3/1994 | Cole |
| 5,297,553 A | 3/1994 | Sliwa et al. |
| 5,304,173 A | 4/1994 | Kittrell et al. |
| 5,305,752 A | 4/1994 | Spivey et al. |
| 5,318,028 A | 6/1994 | Mitchell et al. |
| 5,329,817 A | 7/1994 | Garlick et al. |
| 5,339,282 A | 8/1994 | Kuhn et al. |
| 5,349,954 A | 9/1994 | Tiemann et al. |
| 5,372,138 A | 12/1994 | Crowley et al. |
| 5,398,691 A | 3/1995 | Martin et al. |
| 5,413,108 A | 5/1995 | Alfano |
| 5,415,164 A | 5/1995 | Faupel et al. |
| 5,421,338 A | 6/1995 | Crowley et al. |
| 5,433,202 A | 7/1995 | Mitchell et al. |
| 5,463,548 A | 10/1995 | Asada et al. |
| 5,465,722 A | 11/1995 | Fort et al. |
| 5,474,072 A | 12/1995 | Shmulewitz |
| 5,479,927 A | 1/1996 | Shmulewitz |
| 5,485,839 A | 1/1996 | Aida et al. |
| 5,487,387 A | 1/1996 | Trahey et al. |
| 5,492,126 A | 2/1996 | Hennige et al. |
| 5,501,655 A | 3/1996 | Rolt et al. |
| 5,513,639 A | 5/1996 | Satomi et al. |
| 5,524,630 A | 6/1996 | Crowley |
| 5,546,945 A | 8/1996 | Soldner |
| 5,548,658 A | 8/1996 | Ring et al. |
| 5,553,618 A | 9/1996 | Suzuki et al. |
| 5,558,092 A | 9/1996 | Unger et al. |
| 5,573,497 A | 11/1996 | Chapelon |
| 5,582,173 A | 12/1996 | Li |
| 5,588,032 A | 12/1996 | Johnson et al. |
| 5,590,653 A | 1/1997 | Aida et al. |
| 5,590,657 A | 1/1997 | Cain et al. |
| 5,596,992 A | 1/1997 | Haaland et al. |
| 5,606,971 A | 3/1997 | Sarvazyan |
| 5,609,152 A | 3/1997 | Pellegrino et al. |
| 5,620,479 A | 4/1997 | Diederich |
| 5,640,956 A | 6/1997 | Getzinger et al. |
| 5,643,179 A | 7/1997 | Fujimoto |
| 5,660,185 A | 8/1997 | Shmulewitz et al. |
| 5,664,573 A | 9/1997 | Shmulewitz |
| 5,673,698 A | 10/1997 | Okada et al. |
| 5,678,565 A | 10/1997 | Sarvazyan |
| 5,715,825 A | 2/1998 | Crowley |
| 5,722,411 A | 3/1998 | Suzuki et al. |
| 5,743,863 A | 4/1998 | Chapelon |
| 5,749,364 A | 5/1998 | Sliwa, Jr. et al. |
| 5,759,162 A | 6/1998 | Oppelt et al. |
| 5,762,066 A | 6/1998 | Law et al. |
| 5,766,129 A | 6/1998 | Mochizuki |
| 5,785,663 A | 7/1998 | Sarvazyan |
| 5,787,049 A | 7/1998 | Bates |
| 5,797,849 A | 8/1998 | Vesely et al. |
| 5,800,350 A | 9/1998 | Coppleson et al. |
| 5,810,731 A | 9/1998 | Sarvazyan et al. |
| 5,817,025 A | 10/1998 | Alekseev et al. |
| 5,830,133 A | 11/1998 | Osten et al. |
| 5,833,614 A | 11/1998 | Dodd et al. |
| 5,833,627 A | 11/1998 | Shmulewitz et al. |
| 5,833,633 A | 11/1998 | Sarvazyan |
| 5,833,634 A | 11/1998 | Laird et al. |
| 5,836,882 A | 11/1998 | Frazin |
| 5,836,894 A | 11/1998 | Sarvazyan |
| 5,846,202 A | 12/1998 | Ramamurthy et al. |
| 5,851,182 A | 12/1998 | Sahadevan |
| 5,855,554 A | 1/1999 | Schneider et al. |
| 5,865,167 A | 2/1999 | Godik |
| 5,865,743 A | 2/1999 | Godik |
| 5,891,619 A | 4/1999 | Zakim et al. |
| 5,945,674 A | 8/1999 | Dukor |
| 6,002,958 A | 12/1999 | Godik |
| 6,005,916 A | 12/1999 | Johnson et al. |
| 6,014,473 A | 1/2000 | Hossack et al. |
| 6,023,632 A | 2/2000 | Wilk |
| 6,050,943 A | 4/2000 | Slayton et al. |
| 6,056,690 A | 5/2000 | Roberts |
| 6,078,677 A | 6/2000 | Dolleman et al. |
| 6,083,166 A | 7/2000 | Holdaway et al. |
| 6,102,857 A | 8/2000 | Kruger |
| 6,109,270 A | 8/2000 | Mah et al. |
| 6,117,080 A | 9/2000 | Schwartz |
| 6,135,960 A | 10/2000 | Holmberg |
| 6,146,897 A | 11/2000 | Cohenford et al. |
| 6,149,441 A | 11/2000 | Pellegrino et al. |
| 6,165,734 A | 12/2000 | Garini et al. |
| 6,190,334 B1 | 2/2001 | Lasky et al. |
| 6,242,472 B1 | 6/2001 | Sekins et al. |
| 6,245,017 B1 | 6/2001 | Hashimoto et al. |
| 6,256,090 B1 | 7/2001 | Chen et al. |
| 6,289,235 B1 | 9/2001 | Webber et al. |
| 6,292,682 B1 | 9/2001 | Kruger |
| 6,296,489 B1 | 10/2001 | Blass et al. |
| 6,317,617 B1 | 11/2001 | Gilhuijs et al. |
| 6,351,660 B1 | 2/2002 | Burke et al. |
| 6,368,275 B1 | 4/2002 | Sliwa et al. |
| 6,385,474 B1 | 5/2002 | Rather et al. |
| 6,413,219 B1 | 7/2002 | Avila et al. |
| 6,425,869 B1 | 7/2002 | Rafter et al. |

(56) References Cited

U.S. PATENT DOCUMENTS

| | | |
|---|---|---|
| 6,428,477 B1 | 8/2002 | Mason |
| 6,450,960 B1 | 9/2002 | Rather et al. |
| 6,451,013 B1 | 9/2002 | Bays et al. |
| 6,475,150 B2 | 11/2002 | Haddad |
| 6,478,739 B1 | 11/2002 | Hong |
| 6,490,469 B2 | 12/2002 | Candy |
| 6,511,427 B1 | 1/2003 | Sliwa, Jr. et al. |
| 6,527,759 B1 | 3/2003 | Tachibana et al. |
| 6,540,678 B2 | 4/2003 | Rather et al. |
| 6,559,178 B1 | 5/2003 | Zamoyski |
| 6,574,499 B1 | 6/2003 | Dines et al. |
| 6,587,540 B1 | 7/2003 | Johnson et al. |
| 6,612,988 B2 | 9/2003 | Maor et al. |
| 6,636,584 B2 | 10/2003 | Johnson et al. |
| 6,645,202 B1 | 11/2003 | Pless et al. |
| 6,672,165 B2 | 1/2004 | Rather et al. |
| 6,716,412 B2 | 4/2004 | Unger |
| 6,728,567 B2 | 4/2004 | Rather et al. |
| 6,776,760 B2 | 8/2004 | Marmarelis |
| 6,785,570 B2 | 8/2004 | Nir |
| 6,810,278 B2 | 10/2004 | Webber et al. |
| 6,837,854 B2 | 1/2005 | Moore et al. |
| 6,883,194 B2 | 4/2005 | Corbeil et al. |
| 6,926,672 B2 | 8/2005 | Moore et al. |
| 6,939,301 B2 | 9/2005 | Abdelhak |
| 6,984,210 B2 | 1/2006 | Chambers et al. |
| 7,025,725 B2 | 4/2006 | Dione et al. |
| 7,179,449 B2 | 2/2007 | Lanza et al. |
| 7,285,092 B2 | 10/2007 | Duric et al. |
| 7,346,203 B2 | 3/2008 | Turek et al. |
| 7,497,830 B2 | 3/2009 | Li |
| 7,530,951 B2 | 5/2009 | Fehre et al. |
| 7,556,602 B2 | 7/2009 | Wang et al. |
| 7,570,742 B2 | 8/2009 | Johnson et al. |
| 2001/0029334 A1 | 10/2001 | Graumann et al. |
| 2001/0037075 A1 | 11/2001 | Candy |
| 2001/0051774 A1 | 12/2001 | Littrup et al. |
| 2002/0065466 A1 | 5/2002 | Rather et al. |
| 2002/0099290 A1 | 7/2002 | Haddad |
| 2002/0120196 A1 | 8/2002 | Dubberstein et al. |
| 2002/0131551 A1 | 9/2002 | Johnson et al. |
| 2003/0138053 A1 | 7/2003 | Candy et al. |
| 2004/0030227 A1 | 2/2004 | Littrup et al. |
| 2004/0059265 A1 | 3/2004 | Candy et al. |
| 2004/0152986 A1 | 8/2004 | Fidel et al. |
| 2004/0167396 A1 | 8/2004 | Chambers et al. |
| 2004/0181154 A1 | 9/2004 | Peterson et al. |
| 2005/0165309 A1 | 7/2005 | Varghese et al. |
| 2005/0196025 A1 | 9/2005 | Schofield |
| 2005/0260745 A1 | 11/2005 | Domansky et al. |
| 2006/0009693 A1 | 1/2006 | Hanover et al. |
| 2006/0020205 A1 | 1/2006 | Kamiyama |
| 2006/0064014 A1 | 3/2006 | Falco et al. |
| 2006/0084859 A1 | 4/2006 | Johnson et al. |
| 2006/0085049 A1 | 4/2006 | Cory et al. |
| 2006/0287596 A1 | 12/2006 | Johnson et al. |
| 2006/0293597 A1 | 12/2006 | Johnson et al. |
| 2007/0015949 A1 | 1/2007 | Kaiser |
| 2007/0167823 A1 | 7/2007 | Lee et al. |
| 2008/0045864 A1 | 2/2008 | Candy et al. |
| 2008/0218743 A1 | 9/2008 | Stetten et al. |
| 2008/0229832 A1 | 9/2008 | Huang et al. |
| 2008/0269812 A1 | 10/2008 | Gerber et al. |
| 2008/0275344 A1 | 11/2008 | Glide-Hurst et al. |
| 2008/0281205 A1 | 11/2008 | Naghavi et al. |
| 2008/0294027 A1 | 11/2008 | Frinking et al. |
| 2008/0294043 A1 | 11/2008 | Johnson et al. |
| 2008/0319318 A1 | 12/2008 | Johnson et al. |
| 2009/0035218 A1 | 2/2009 | Ross et al. |
| 2009/0076379 A1 | 3/2009 | Hamill et al. |
| 2009/0129556 A1 | 5/2009 | Ahn |
| 2009/0143674 A1 | 6/2009 | Nields et al. |
| 2010/0331699 A1 | 12/2010 | Yu et al. |
| 2011/0152685 A1 | 6/2011 | Misono |
| 2013/0267850 A1 | 10/2013 | Berman |
| 2014/0316269 A1 | 10/2014 | Zhang et al. |

FOREIGN PATENT DOCUMENTS

| | | |
|---|---|---|
| EP | 0097917 A | 1/1984 |
| EP | 284055 A | 9/1988 |
| EP | 317049 A | 5/1989 |
| EP | 320444 A | 6/1989 |
| EP | 351610 A | 1/1990 |
| EP | 538241 A | 4/1993 |
| EP | 0609922 A | 8/1994 |
| EP | 614651 A | 9/1994 |
| EP | 642762 A | 3/1995 |
| EP | 661029 A | 7/1995 |
| EP | 774276 A | 5/1997 |
| EP | 1063920 A | 1/2001 |
| GB | 2040642 A | 8/1980 |
| JP | 2005253827 A | 9/2005 |
| JP | 2007181679 A | 7/2007 |
| JP | 2009034521 A | 2/2009 |
| WO | 9947046 | 9/1999 |
| WO | 9947046 A | 9/1999 |
| WO | 0228350 | 4/2002 |
| WO | 0230288 A | 4/2002 |
| WO | 2004061743 A | 7/2004 |
| WO | 2005057467 A | 6/2005 |
| WO | 2007023408 A | 3/2007 |

OTHER PUBLICATIONS

Barlow et al., "Prospective Breast Cancer Risk Prediction Model for Women Undergoing Screening Mammogrpahy," J. Nat'l Cancer Institute 98(17): 1204-1214 (2006).

Boone et al., "Dedicated Breast CT: Radiation Dose and Image Quality Evaluation," Med Phys 221(3): 657-667 (2001).

Boston et al., "Estimation of the Content of Fat and Parenchyma in Breast Tissue Using MRI T1 Histograms and Phantoms," MRI 23: 591-599 (2005).

Boyd, "Quantitative Classification of Mammographic Densities and Breast Cancer Risk: Results from the Canadian National Breast Screening Study," J Nat'l Cancer Institute 87(9): 670-675 (1995).

Byng et al., The Quantitative Analysis of Mammographic Densities,: Phys Med Biol 39 (1994) 1629-1638.

Cadzow, "Signal enhancement—A composite property mapping algorithm," IEEE Transactions on Acoustics, Speech and Signal Processing 36(1) (1988) 49-62.

Centerline, PortalVision section, Summer 2002 edition, published by Varian Medical Systems.

Chang et al., "Breast Density Analysis in 3-D Whole Breast Ultrasound Images," IEEE Proc 28th IEEE EMBS Annual International Conference (2006) 2795-2798.

Chang et al., Kirchhoff migration of ultrasonic images, Materials evaluation, V59, N3, 413-417, 2001.

Chelfouh et al., "Characterization of Urinary Calculi: in Vitro Study of 'Twinking Artifact' revealed by Color-Flow Sonography," AJR Am. J. Roentgenol. 171( 4) (1998) 1055-60.

Chen et al., "Projecting Absolute Invasive Breast Cancer Risk in White Women with a Model that Includes Mammographic Density," J. Nat'l Cancer Institute 98(17) (2006) 1215-1226.

Diederich et al., "The design of ultrasound applicators for interstitial hyperthermia," Ultrasonics Symposium, Proc IEEE 1993 Baltimore, MD, USA Oct. 31-Nov. 3, 1993, New York, NY, USA, 1215-1219.

Drineas et al., "Distance matrix reconstruction from incomplete distance information for sensor network localization," 3rd Annual IEEE Communications Society on Sensor and Ad Hoc Communications and Networks, Sep. 2006, pp. 536-544.

Duric et al. "Computed Ultrasound Risk Evaluation," Barbara Ann Karmanos Cancer Institute. pp. 1-23. 2008.

(56) References Cited

OTHER PUBLICATIONS

Duric et al., "Detection of Breast Cancer with Ultrasound Tomography: First Results with the Computed Ultrasound Risk Evaluation (CURE) Prototype," Med Phys 34(2) (2007).
Dussik, "The Ultrasonic Field as a Medical Tool," Amer J Phys Med 33(1) (1954) 5-20.
Fjield et al., "A Parametric Study of the Concentric-Ring Transducer Design for MRI Guided Ultrasound Surgery," J. Acoust. Soc. America 100 (2) Pt. 1 (1996).
Gervias et al., "Renal Cell Carcinoma: Clinical Experience and Technical Success with Radio-frequency Ablation of 42 Tumors," Radiology 226 (2003) 417-424.
Glide et al., "Novel Approach to Evaluating Breast Density Utilizing Ultrasound Tomography," Med Phys 34(2) (2007) 744-753.
Glide, "A Novel Approach to Evaluating Breast Density Using Ultrasound Tomography," Dissertation Graduate School of Wayne State University (2007).
Glide-Hurst et al., "A Novel Ultrasonic Method for Measuring Breast Density and Breast Cancer Risk," Med Imaging 2008, Proc SPIE vol. 6920, 69200Q.
Glide-Hurst, "A New Method for Quantitative Analysis of Mammographic Density," Med Phys 34(11) (2007) 4491-4498.
Greenleaf et al., "Artificial Cavitation Nuclei Significantly Enhance Acoustically Incuded Cell Transfection," Ultrasound Med & Biol 24 (1998) 587-595.
Greenleaf, "Computerized Tomography with Ultrasound," Proc IEEE 71(3) (1983) 330-337.
Hayashi, "A New Method of Measuring in Vivo Sound Speed in the Reflection Mode," J Clin Ultrasound 16(2) (1988) 87-93.
Jellins et al., "Velocity Compensation in Water-Coupled Breast Echography," Ultrasonics 11(5) (1973) 223-6.
Kaizer et al., "Ultrasonographically Defined Parenchymal Pattenrs of the Breast: Relationship to Mammographic Patterns and Other Risk Factors for Breast Cancer," Brit J Radiology 61(722) (1988) 118-24.
Karssemeijer, "Automated Classification of Parenchymal Patterns in Mammograms," Phys Med Biol 43 (1998) 365-378.
Kerlikowske et al., "Longitudinal Measurement of Clinical Mammographic Breast Density to Improve Estimation of Breast Cancer Risk," J. Nat'l Cancer Institute 99(5) (2007) 386-395.
Klimes, Grid Travel-time Tracing: Second-order Method for the First Arrivals in Smooth Media, PAGEOPH, vol. 148, Nos. 3/4,1996.
Knapp et al., "The generalized correlation method for estimation of time delay," IEEE Transactions on Acoustics, Speech and Signal Processing 24(4) (1976) 320-327.
Kossoff et al., "Average Velocity of Ultrasound in the Human Female Breast," J Acoust Soc America 53(6) (1973) 1730-6.
Li et al., "Clinical Breast Imaging Using Sound-Speed Reconstructions of Ultrasound Tomography Data," Med Imaging 2008, Proc SPIE vol. 6920, 6920009.
Li et al., Breast Imaging Using Transmission Ultrasound: Reconstructing Tissue Parameters of Sound Speed and Attenuation,2008 International Conference on BioMedical Engineering and Informatics, IEEE computer society, 708-712.
Li et al., Comparison of ultrasound attenuation tomography methods for breast imaging, Medical Imaging 2008: UltrasonicImaging and Signal Processing, Proc. of SPIE vol. 6920, 692015-(1-9), 2008.
Li et al., Refraction corrected transmission ultrasound computed tomography for application in breast imaging, Med. Phys. 37(5), May 2010, 2233-2246.
Louvar et al., "Correlation of Color Doppler Flow in the Prostate with Tissue Microvascularity," Cancer 1:83(1) (1998) 135-40.
Marias, "Automatic Labelling and BI-RADS Characterisation of Mammogram Densities," Proc 2005 IEEE, Sep. 1-4, 2005, pp. 6394-6398.
Mast, "Empirical Relationships Between Acoustic Parameters in Human Soft Tissues," Acoust Research Letters Online, Nov. 16, 2000, pp. 37-42.

Masugata et al., "Relationship Between Myocardial Tissue Density Measured by Microgravimetry and Sound Speed Measured by Acoustic Microscopy," Ultrasound in Med & Biol 25(9) (1999) 1459-1463.
Metz, "Basic principles of ROC analysis"; Semin Nucl Med. Oct. 8, 1978 (4):283-98.
Metz, "Receiver Operating Characteristic Analysis: A Tool for the Quantitative Evaluation of Observer Performance and Imaging Systems"; J Am Coli Radiol 2006; 3: 413-422.
Metz, "ROC methodology in radiologic imaging"; Invest Radiol. Sep, 21 1986 (9):720-33.
Miller et al., "Sonoporation of Cultured Cells in the Rotating Tube Exposure System," Ultrasound Med & Biol 25 (1999) 143-149.
Noble et al., "Spleen Hemostasis Using High-Intensity Ultrasound: Survival and Healing," J. Trauma Injury, Infection, and Critical Care 53(6) (2002) 1115-1120.
Ophir et al., "Elastography: Ultrasonic Estimation and Imaging of the Elastic Properties of Tissues," Proc Instn Mech Engrs 213(Part H) (1999) 203-233.
Palomares et al., "Mammographic Density Correlation with Gail Model Breast Cancer Risk Estimates and Component Risk Factors," Cancer Epidemiol Biomarkers Prev 15(7) (2006) 1324-1330.
Robinson et al., "Quantitative Sonography," Ultrasound in Med & Biol 12(7): 555-65 (1986).
Teubner et al., "Comparative Studies of Various Echomammography," Ultraschall in Der Medizin 3(3) (1982) 109-18, G. Thieme Verlag, Stuttgart/New York.
Chan et al., An Agglomeration Multigrid Method for Unstructured Grids, Contemporary Mathematics, vol. 218, 1998.
McCormick et al., Multigrid solution of a linearized, regularized least-squares problem in electrical impedance tomography, Inverse Problems 9, 1993, 697-713.
Oh et al., Multigrid Tomographic Inversion With Variable Resolution Data and Image Spaces, IEEE Transactions on Image Proessing, vol. 15, No. 9, Sep. 2006.
Quan et al., Sound-speed tomography using first-arrival transmission ultrasound for a ring array, Medical Imaging 2007: Ultrasonic Imaging and Signal Processing, Proc. of SPIE vol. 6513.
Zhang et al., A comparison of material classification techniques for ultrasound inverse imaging, J. Acoust. Soc. Am. 111 (1), Pt. 1, Jan. 2002.
Andre et al., "A New Consideration of Diffraction Computed Tomography for Breast Imaging: Studies in Phantoms and Patients," Acoustical Imaging, 21, 379 (1995).
Candy et al., "Signal Processing: The Model-Based Approach," pp. 178-213 (McGraw Hill, 1986).
Greenleaf et al., "Multidimensional Visualization of Ultrasonic Images," J Acoust Soc Amer 95 (1994) 2902.
Greenleaf et al., "Introduction to Computer Ultrasound Tomography," Computer Aided Tomography and Ultrasonics in Medicine, (1970) North-Holland 125-136.
Harmuth, "Sequency Theory: Foundations and Applications, Advances in Electronics and Electron Physics," (Academic Press, 1977) 18-95.
Haykin, "Neural Networks—A Comprehensive Foundation," Prentice Hall (1998) 236-284.
Hebden et al., "Acoustically Modulated Electrical Impedance Tomography," Proc SPIE 1231 (1990) 7-14.
Jellins, "Breast Tissue Characterization" Tissue Characterization with Ultrasound 2 (1986) CRC Press 95-122.
Mitchell, An Introduction to Genetic Algorithms, pp. 8-11, 35-78, 155-179 (MIT Press, 1996).
Nelson et al., "Interactive Acquisition, Analysis and Visualization of Sonographic Volume Data," International J Imaging Sys and Tech 8(26) (1997) 26-37.
Sehgal et al., "Visualization of Breast Calcification by Acoustic Resonance Imaging," Radiology Supplement, 84th Scientific Assembly and Annual Meeting, Nov. 29-Dec. 4, 1998 presented in McCormick Place, Chicago, Illinois, vol. 209, listing: 1150 (1998).
Shi et al., "Effects of Pressure Changes on Harmonic and Subharmonic Response of US Contrast Microbubbles," 84th Sci-

(56) References Cited

OTHER PUBLICATIONS entific Assembly and Annual Meeting, Nov. 29-Dec. 4, 1998, presented in McCormick Place, Chicago, Illinois, vol. 209, listing: 1154 (1998).
Glide-Hurst et al., "Volumetric breast density evaluation from ultrasound tomography images", Medical Physics, vol. 35, 2008, pp. 3988-3997.
Li et al., "In Vivo Breast Sound-Speed Imaging with Ultrasound Tomography", Ultrasound in Med & Bioi., vol. 35, No. 10, 2009, pp. 1615-1628.
Banihashemi, B. et al., "Ultrasound Imaging of Apoptosis in Tumor Response: Novel Preclinical Monitoring of Photodynamic Therapy Effects." Cancer Research, vol. 68, No. 20, Oct. 15, 2008, pp. 8590-8596.
Singh, Seema et al. "Color Doppler Ultrasound as an Objective Assessment Tool for Chemotherapeutic Response in Advanced Breast Cancer." Breast Cancer, 2005, vol. 12, No. 1, 2005, pp. 45-51.
Yaman, C. et al., "Three-Dimensional Ultrasound to Assess the Response to Treatment in Gynecological Malignancies." Gynecologic Oncology, Academic Press, vol. 97, No. 2, May 1, 2005, pp. 665-668.
Vaezy et al., "Real-Time Visualization of High-Intensity Focused Ultrasound Treatment Using Ultrasound Imaging," Ultrasound in Med & Biol 27(1) (2001) 33-42.
Walach et al., Local Tissue Attenuation Images Based on Pulsed-Echo Ultrasound Scans, IEEE Transactions onBiomedical Engineering, vol. 36. No. 2, Feb. 1989.
Wei et al., "Correlation Between Mammographic Density and Volumetric Fibroglandular Tissue Estimated on Breast MR Images," Med Phys 31(4) (2004) 933-942.
Weiwad et al., "Direct Measurement of Sound Velocity in Various Specimens of Breast Tissue," Invest Radiol 35(12) (2000) 721-6.
Wolfe, "Risk for Breast Cancer Development Determined by Mammographic Parenchymal Pattern," Cancer 37(5) (1976) 2486-2493.
Xu, et al. "A Study of 3-Way Image Fusion for Characterizing Acoustic Properties of Breast Tissue." Medical Imaging 2008: Ultrasonic Imaging and Signal Processing. Feb. 16, 2008.
Yaffe, "Breast Cancer Risk and Measured Mammographic Density," Eur J Cancer Prevention 7(1) (1998) S47-55.
Yankelevitz et al., "Small Pulmonary Nodules: Volumetrically Determined Growth Rates Based on CT Evaluation," Radiology 217 (2000) 251-256.

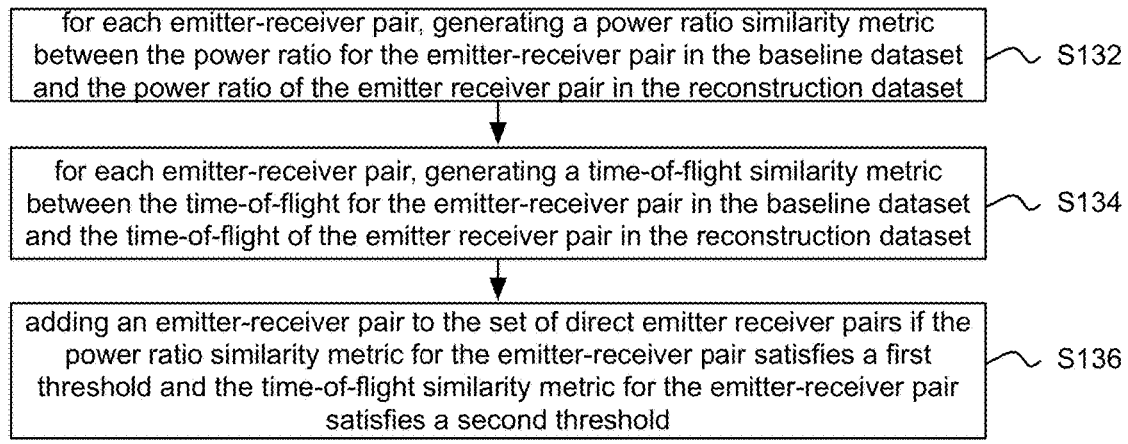
FIGURE 2
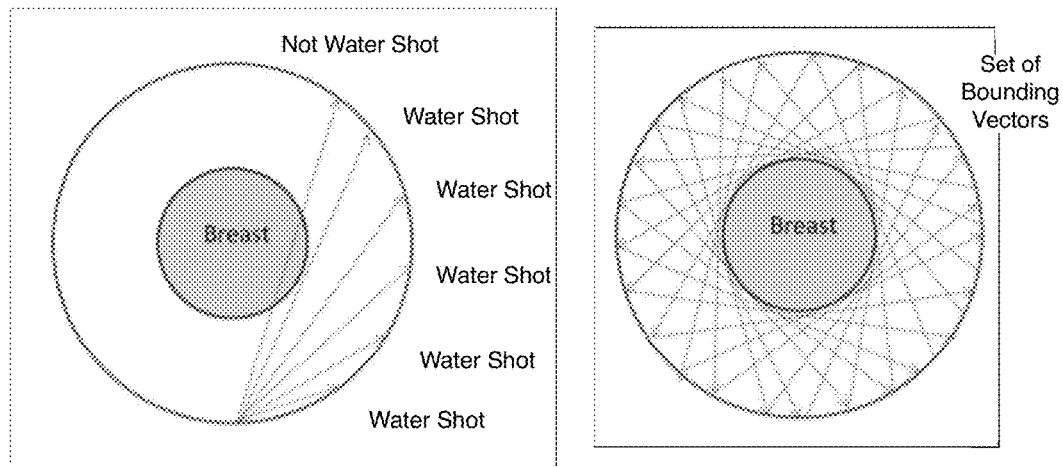
FIGURE 3
FIGURE 4A
FIGURE 4B

METHOD AND SYSTEM FOR IMAGING A VOLUME OF TISSUE WITH TISSUE BOUNDARY DETECTION

CROSS-REFERENCE TO RELATED APPLICATIONS

This application claims the benefit of U.S. Provisional Application Ser. No. 61/694,999 filed 30 Aug. 2012, which is incorporated in its entirety herein by this reference.

TECHNICAL FIELD

This invention relates generally to the medical imaging field, and more specifically to a new and useful method and system for imaging a volume of tissue with tissue boundary detection.

BACKGROUND

Early detection and treatment of breast cancer and other kinds of cancer typically result in a higher survival rate. Despite a widely accepted standard of mammography screenings for breast cancer detection, there are many reasons that cancer is often not detected early. One reason is low participation in breast screening, as a result of limited access to equipment and fear of radiation and discomfort. Another reason is limited performance of mammography, particularly among women with dense breast tissue, who are at the highest risk for developing breast cancer. As a result, many cancers are missed at their earliest stages when they are the most treatable. Furthermore, mammography results in a high rate of "false alarms", leading to unnecessary biopsies that are collectively expensive and result in emotional duress in patients.

Other imaging technologies in development are unlikely to create a paradigm shift toward early detection of cancer. For example, magnetic resonance (MR) imaging can improve on some of these limitations by virtue of its volumetric, radiation-free imaging capability, but requires long exam times and use of contrast agents. Furthermore, MR has long been prohibitively expensive for routine use. Conventional sonography is not a practical alternative because of its operator dependence and the long time needed to scan the whole breast. In other words, lack of a low-cost, efficient, radiation-free, and accessible tissue imaging alternative to mammography is a barrier to dramatically impacting mortality and morbidity through improved screening.

Thus, there is a need in the medical imaging field to create a new and useful method and system for imaging a volume of tissue that addresses the need to combine the low-cost advantage of mammography with superior imaging performance. This invention provides such a useful method and system.

BRIEF DESCRIPTION OF THE FIGURES

FIGS. 1-3 are flowcharts depicting an embodiment of a method for imaging a volume of tissue;

FIGS. 4A and 4B are schematics of an embodiment of a method for imaging a volume of tissue;

DESCRIPTION OF THE PREFERRED EMBODIMENTS

The following description of preferred embodiments of the invention is not intended to limit the invention to these preferred embodiments, but rather to enable any person skilled in the art to make and use this invention.

1. Method

Figure 1:
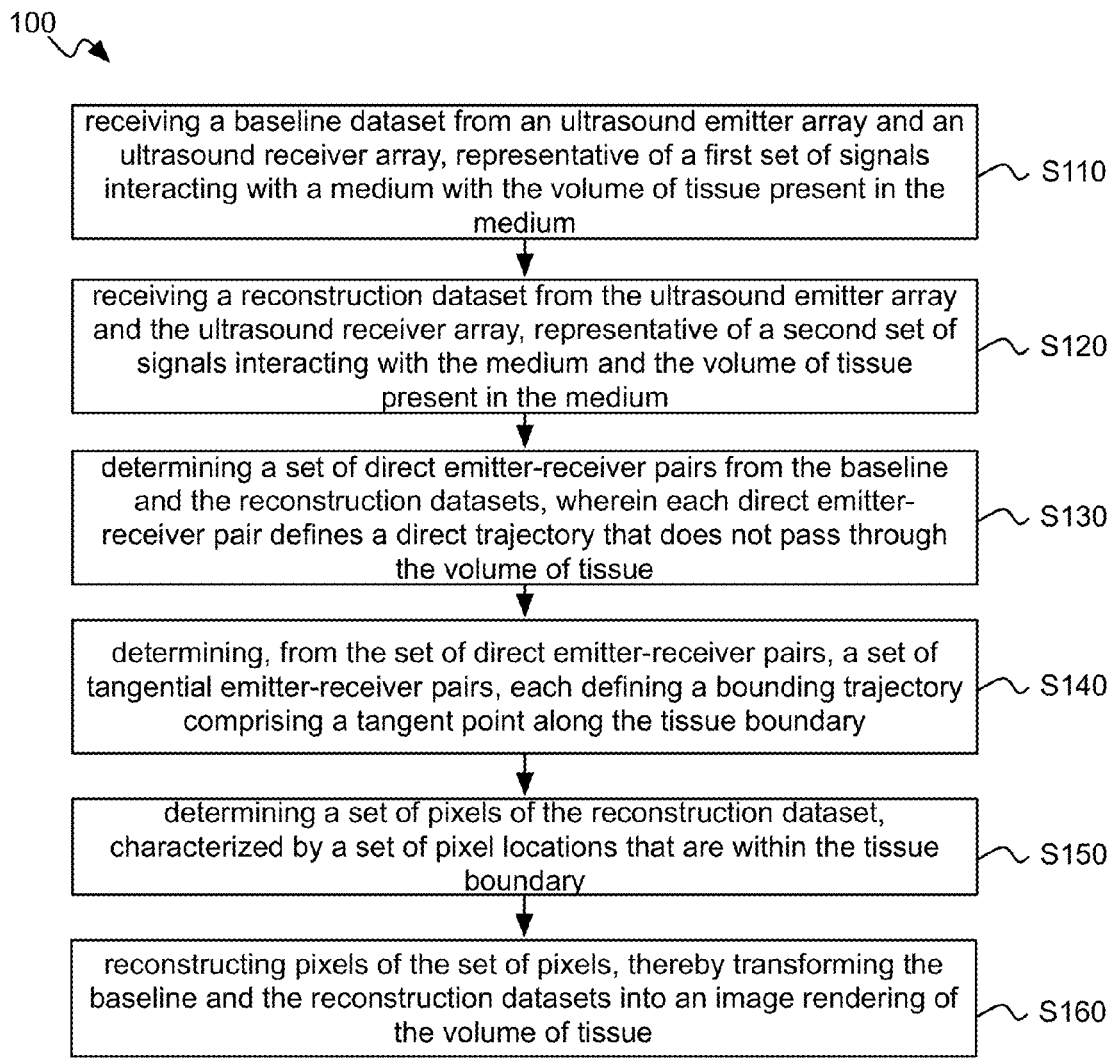

As shown in FIG. 1, an embodiment of a method 100 for imaging a volume of tissue and defining a tissue boundary comprises: receiving a baseline dataset from an ultrasound emitter array and an ultrasound receiver array, representative of a first set of signals interacting with a medium without the volume of tissue present in the medium S110; receiving a reconstruction dataset from the ultrasound emitter array and the ultrasound receiver array, representative of a second set of signals interacting with the medium and the volume of tissue present in the medium S120; determining a set of direct emitter-receiver pairs from the baseline and the reconstruction datasets, wherein each direct emitter-receiver pair defines a direct trajectory that does not pass through the volume of tissue S130; and determining, from the set of direct emitter-receiver pairs, a set of tangential emitter-receiver pairs, each defining a bounding vector comprising a tangent point along the tissue boundary S140. The method 100 can additionally comprise determining a set of interior pixels of the reconstruction dataset, characterized by a set of pixel locations that are within the tissue boundary S150; and reconstructing pixels of the set of pixels, thereby transforming the baseline and the reconstruction datasets into an image rendering of the volume of tissue S160. The method 100 is preferably used to image a scan region including a tissue boundary surrounded by a medium (e.g., a fluid medium), wherein the scan region defines a two-dimensional imaging plane. Thus, each of these steps or blocks is preferably performed for a cross-sectional, two-dimensional image "slice" of the volume of tissue, and repeated for multiple cross-sectional slices of the tissue (e.g., during a scan of a volume of tissue). However, other variations of the method 100 can additionally or alternatively be performed for volumetric, three-dimensional imaging of the tissue.

In implementing a portion of an embodiment of the method 100, the transducer array preferably includes a plurality of ultrasound emitters that emit acoustic signals toward the scan region and a plurality of ultrasound receivers that detect the emitted acoustic signals after the acoustic signals interact with objects in their respective signal paths. The plurality of ultrasound emitters and the plurality of ultrasound receivers can define a plurality of emitter-receiver pairs, each emitter-receiver pair corresponding to a signal path intersecting the medium and/or the volume of tissue. Preferably, the method 100 generates an image rendering of the volume of tissue, based upon a selective reconstruction process that can, for example, be based upon acoustic attenuation, acoustic reflection, acoustic speed, and/or any suitable acoustic parameter derived from the interaction between emitted acoustic signals and the volume of tissue. In alternative embodiments, the method 100 can use any suitable acoustic parameter derived from emitted and reflected acoustic signals to distinguish the boundaries between two differing non-mixing substantially homogenous fluids, differing substantially homogenous elastic media, or combinations of the two.

The method 100 preferably also provides a rapid, easy-to-use, ultrasound imaging process that effectively identifies a tissue boundary of the volume of tissue and enables differentiation between an image pixel location within the tissue boundary and an image pixel location outside of the tissue boundary. Such a differentiation can also be described as defining a binary "mask" which represents whether a given pixel is inside or outside of the tissue. For example, the mask preferably enables faster image rendering times, and therefore shorter scans and patient exams without sacrificing image quality, since only pixels known to be within the tissue boundary are required to be reconstructed to create an image rendering of the tissue. Furthermore, a determination that no pixels of a given imaging plane are within the tissue boundary, based upon processing of the binary mask, can be used as an indicator to detect the end of a scan (e.g., when imaging a volume of breast tissue in a posterior-anterior direction from the chest wall to the nipple). In one variation, the method 100 can be used to image breast tissue, and in other variations, the method 100 can additionally or alternatively be used to image any suitable kind of tissue surrounded by a medium and an imaging transducer.

Block S110 recites receiving a baseline dataset from an ultrasound emitter array and an ultrasound receiver array, representative of a first set of signals interacting with a medium without the volume of tissue present in the medium. Block S110 functions to receive baseline data representative of the acoustic parameters of the medium alone within the scan region of the transducer. Preferably, the medium is a fluid medium (e.g., water), however, the medium can alternatively be a non-fluid medium (e.g., gas, polymer in a gel phase, solid). Furthermore, the medium is preferably homogenous, such that the baseline dataset can include any particular two-dimensional scan region within the medium and can be considered representative of any other two-dimensional scan region within the medium; however, the baseline dataset can alternatively comprise respective data for each two-dimensional scan region in the scan volume accessible by the transducer (e.g., when using a non-homogenous medium). Additionally, Block S110 preferably includes receiving data directly from the transducer, which preferably includes a plurality of ultrasound emitters and a plurality of ultrasound receivers that define a scan region (e.g., a two-dimensional imaging plane) surrounded by a perimeter defined by the transducer. However, the transducer can alternatively have any suitable shape and surround a scan region including any suitable acoustic coupling medium. In other variations, Block S110 can additionally or alternatively include receiving data from a computer-readable medium or storage, such as a server, cloud storage, hard drive, flash memory, optical device (CD or DVD), or other suitable device capable of receiving, storing, and/or otherwise transferring acoustic baseline data. For example, in one variation, baseline data can be obtained during calibration of the emitter-receiver pairs, and can be stored on and/or transmitted from a storage module for further processing in other method blocks.

Preferably, the baseline dataset in Block S110 includes power ratio data (representing attenuation of the ultrasound signal traveling through the medium) and time-of-flight data (representing a speed at which the ultrasound signal travels through the fluid medium) between each ultrasound emitter in the ultrasound emitter array and each ultrasound receiver in the ultrasound receiver array. The baseline dataset is thus preferably organized into a power ratio matrix and a time-of-flight matrix for one or more two-dimensional scan regions of the transducer. Each matrix preferably has dimensions n by m, where n=number of emitters in the transducer array and m=number of receivers in the transducer array, thereby defining n by m emitter-receiver pairs configured to surround the volume of tissue; the parameters n and m can be equal or unequal to each other. In other words, for each slice of the transducer scan volume that will reconstructed for tissue imaging, Block S110 preferably receives, or enables generation of, a corresponding power ratio matrix and time-of-flight matrix. The matrices for one slice of the transducer scan volume can be duplicated for every slice (e.g., if the fluid medium is homogenous), and/or matrices for each of multiple slices of the transducer scan volume can be independently derived. In other variations, the baseline dataset can additionally or alternatively include any other acoustic signal parameter and can be arranged for processing in any other suitable manner.

In an example of Block S110, the transducer array is a circular or ellipsoidal ring array submerged in a tank of water (i.e., the medium) and configured to sequentially move along an axis perpendicular to a plane defined by the transducer in discrete steps, scanning a two-dimensional scan region at each discrete step. The fluid medium in the example is homogeneous within the tank of water, such that the baseline dataset can include any particular two-dimensional scan region within the fluid medium and can be considered representative of any other two-dimensional scan region within the fluid medium. The transducer array in the example comprises 2048 ultrasound emitter elements and 2048 ultrasound receiver elements, spaced evenly about the scan region and configured to generate power ratio and time of flight data, such that a 2048×2048 power ratio matrix and a 2048×2048 time of flight matrix can be generated for each imaging plane.

Block S120 recites receiving a reconstruction dataset from the ultrasound emitter array and the ultrasound receiver array, representative of a second set of signals interacting with the medium and the volume of tissue present in the medium. Block S120 functions to receive acoustic data comprising information from which boundary information of the volume of tissue and acousto-mechanical characteristics of the volume of tissue can be derived. In particular, the reconstruction dataset preferably characterizes interactions between the acoustic signals emitted by the ultrasound emitters and the volume of tissue within the medium, including information such as scattering, reflection, refraction, diffusion, and transmission of the acoustic signal off and through the tissue. Preferably, the reconstruction dataset is generated and/or received in a manner similar to that for the baseline dataset in Block S110, with the only difference being the presence of the volume of tissue within the medium. Thus, the reconstruction dataset is also preferably organized into a power ratio matrix and a time-of-flight matrix (each having dimensions n by m) for one or more two-dimensional scan regions of the transducer. However, the reconstruction dataset can comprise any suitable type of data and can be generated and/or received in any suitable manner that allows a tissue boundary to be determined from the baseline and the reconstruction datasets.

Figure 7:
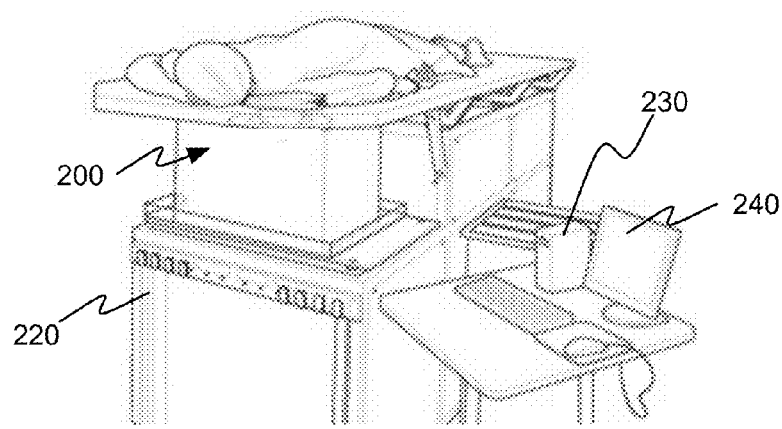
FIGS. 7, 8A, and 8B are schematics of an embodiment of a system for imaging a volume of tissue.

Similar to receiving the baseline dataset in Block S110, Block S120 can include receiving the reconstruction dataset directly from the transducer array, or can include receiving data from a computer-readable medium or storage, such as a server, cloud storage, hard drive, flash memory, optical device (CD or DVD), or other suitable device capable of receiving, storing, and/or otherwise transferring data. In one example for imaging a volume of breast tissue, the reconstruction dataset is gathered during a scan of a patient lying prone on his or her stomach on a scanner table having an aperture. The table in the example contours to the body of the patient, thereby increasing scanning access to the axilla regions of the breast and increasing patient comfort. The aperture in the table further allows the breast to extend through the table and be submerged in an imaging tank filled with water or another suitable acoustic coupling medium that propagates acoustic waves. As shown in FIG. 7, a ring-shaped transducer with transducer elements (emitters and receivers) is located within the imaging tank of the example and encircles the breast. During the scan, the ring transducer passes along the tissue, in an anterior-posterior direction between the chest wall and the nipple region of the breast to acquire an acoustic data set including measurements such as acoustic reflection, acoustic attenuation, and acoustic speed, at discrete scanning steps or coronal "slices".

Block S130 recites determining a set of direct emitter-receiver pairs from the baseline and the reconstruction datasets, wherein each direct emitter-receiver pair defines a direct trajectory that does not pass through the volume of tissue. The direct emitter-receiver pairs are preferably selected from the set of n by m emitter-receiver pairs defined in Blocks S110 and S120, such that S130 distinguishes between emitter-receiver pairs defining trajectories passing through the volume of tissue and emitter-receiver pairs defining trajectories not passing through the volume of tissue. Block S130 thus functions to map which emitter-receiver pairs form signal paths or trajectories that are uninterrupted by the scanned volume of tissue, within each imaging plane. For a variation in which the medium is water, acoustic signals passing between the direct emitter-receiver pairs are direct trajectory "water shots" passing through, and only through, water, as shown in FIG. 4A.

As shown in FIG. 2, Block S130 preferably includes: for each emitter-receiver pair, generating a power ratio similarity metric between the power ratio for the emitter-receiver pair in the baseline dataset and the power ratio for the emitter-receiver pair in the reconstruction dataset S132; for each emitter-receiver pair, generating a time-of-flight similarity metric between the time-of-flight for the emitter-receiver pair in the baseline dataset and the time-of-flight for the emitter-receiver pair in the reconstruction dataset S134; and adding an emitter-receiver pair to the set of direct emitter-receiver pairs if the power ratio similarity metric for the emitter-receiver pair satisfies a first threshold and the time-of-flight similarity metric for the emitter-receiver pair satisfies a second threshold S136. In other variations, Block S130 can alternatively comprise determining the set of direct emitter-receiver pairs in any suitable manner, such as by determining which emitter-receiver pairs define trajectories through the volume of tissue, and excluding them from the set of direct emitter-receiver pairs. Furthermore, Block S130 can additionally or alternatively comprise generating comparisons between any other suitable metric from the baseline and the reconstruction datasets, in a manner that identifies direct emitter-receiver pairs within the set of emitter-receiver pairs.

Block S132 recites for each emitter-receiver pair, generating a power ratio similarity metric between the power ratio for the emitter-receiver pair in the baseline dataset and the power ratio for the emitter-receiver pair in the reconstruction dataset; Block S134 recites for each emitter-receiver pair, generating a time-of-flight similarity metric between the time-of-flight for the emitter-receiver pair in the baseline dataset and the time-of-flight for the emitter-receiver pair in the reconstruction dataset. Blocks S132 and S134 collectively function to determine whether the signal path or trajectory between the emitter and receiver of each emitter-receiver pair is uninterrupted by tissue. For each emitter-receiver pair, Block S132 preferably determines a difference between the power ratio of the baseline dataset (corresponding to a signal known to have a trajectory through the medium only) and the power ratio of the reconstruction dataset (corresponding to a signal with a trajectory either through the medium only or through both the volume of tissue and the medium), such that the difference is a similarity metric that can be used to determine the trajectory defined by the emitter-receiver pair. The difference in power ratios can then be compared to a first threshold in Block S136 to determine if the power ratio of the baseline dataset is substantially similar to the power ratio for the reconstruction dataset (i.e., the power ratios of the baseline dataset and the reconstruction dataset, corresponding to a given emitter-receiver pair, are similar within a given tolerance). Similarly, for each emitter-receiver pair, Block S134 preferably determines a difference between the time-of-flight for the emitter-receiver pair in the baseline dataset and the time-of-flight for the emitter-receiver pair in the reconstruction dataset. The difference in time-of-flights can then be compared to a second threshold in Block S136 to determine if the time-of-flight of the baseline dataset is substantially similar to the time-of-flight for the reconstruction dataset (i.e., the time of flights of the baseline dataset and the reconstruction dataset, corresponding to a given emitter-receiver pair, are similar within a given tolerance). The similarity metrics in Blocks S132 and S134 can comprise differences (e.g., arithmetic differences, percentage differences) and/or any other suitable metric that can be compared to thresholds in Block S136.

Block S136 recites adding an emitter-receiver pair to the set of direct emitter-receiver pairs if the power ratio similarity metric for the emitter-receiver pair satisfies a first threshold and the time-of-flight similarity metric for the emitter-receiver pair satisfies a second threshold. Block S136 functions to generate the set of direct emitter-receiver pairs, wherein a direct emitter-receiver pair is defined as an emitter-receiver pair having a signal path or direct trajectory that passes only through the fluid medium. In a preferred embodiment, a particular emitter-receiver pair is considered to be a direct emitter-receiver pair if both its power ratio and time-of-flight for the baseline and reconstruction datasets are determined (through Blocks S132 and S134) to have similarity metrics that satisfy respective thresholds. For example, power ratio differences can be compared to a first threshold, and time-of-flight differences can be compared to a second threshold, in order to decide if a given emitter-receiver pair is a direct emitter-receiver pair. However, Block S136 can include adding the emitter-receiver pair to the set of direct emitter-receiver pairs if any suitable combination of parameters is considered to be substantially similar or equal between the baseline and the reconstruction datasets. In one variation, the dataset of direct emitter-receiver pairs based upon information from block S130 is organized into a binary logic matrix forming a truth table that is n by m in size. Each element of the matrix, corresponding to an emitter-receiver pair, represents whether the signal between the emitter-receiver pair corresponding to that element is a direct, uninterrupted signal path ("water shot"). However, the data can be organized in any suitable manner.

In some variations or examples, Block S130 of determining a set of direct emitter-receiver pairs can include only a portion of Blocks S132, S134, and/or S136, in the interest of further reducing processing time. In one example, a direct emitter-receiver satisfies both Condition A of similar power ratios and Condition B of similar time-of-flight between the baseline dataset and reconstruction dataset as determined from the similarity metrics and the first and second thresholds. In this example, if a particular emitter-receiver pair is already known to not satisfy Condition A, then that particular emitter-receiver pair cannot be considered a direct emitter-receiver pair, regardless of whether it satisfies Condition B. Therefore, if Block S132 and a portion of Block S136 determine that a particular emitter-receiver pair does not satisfy Condition A, then Block S134 and a portion of Block S136, for checking Condition B, do not have to be performed. In another variation, a determination that Condition B is not satisfied can be used to skip performance of a check for Condition A, in order to reduce processing time. In other variations, the method 100 can altogether omit generating multiple similarity metrics and comparing the multiple similarity metrics to thresholds, such that the set of direct emitter-receiver pairs is determined based upon generation of a single similarity metric and the comparing the single similarity metric to a threshold in order to identify an emitter-receiver pair as a direct emitter-receiver pair. In still other variations, the method 100 can comprise generating more than two similarity metrics for different acoustic parameters, comparing the more than two similarity metrics to respective thresholds, and identifying an emitter-receiver pair as a direct emitter-receiver pair only if all similarity metrics satisfy their respective threshold conditions.

Block S140 recites determining, from the set of direct emitter-receiver pairs, a set of tangential emitter-receiver pairs, each defining a bounding vector comprising a tangent point along the tissue boundary. Block S140 functions to define a set of tangential vectors, each drawn between respective emitter-receiver pairs, wherein each tangential vector defines a tangent point along the tissue boundary. As shown in FIG. 4B, a set of such tangential vectors or signal paths, collectively outline the tissue boundary within an imaging plane of the volume of tissue, particularly if the breast tissue is convex. A higher number of emitters (and possible number of emitter-receiver pairs) preferably generally improves the resolution of the defined tissue boundary, by producing a greater number of tangent points that form the tissue boundary.

As shown in FIG. 3, block S140 preferably includes, for each emitter, methodically determining a receiver forming an emitter-receiver pair that defines a trajectory that is tangential (or is closest to being tangential) to the tissue boundary S142. In one example, as shown in FIG. 4A, Block S142 includes considering whether a first receiver adjacent to an emitter forms an emitter-receiver pair that is in the set of direct emitter-receiver pairs. The method 100 preferably checks whether the signal between the emitter and the first receiver is a "water shot" as represented in the binary logic matrix generated in Block S130 or information gathered in block S130. If this first receiver forms a direct emitter-receiver pair with the emitter, then Block S142 similarly repeats this check for progressively distant receivers from the emitter (in a particular checking direction) against the binary logic matrix (or other information) until finding an indirect receiver that does not form a direct emitter-receiver pair (i.e., an indirect emitter-receiver pair that does not define a "water shot" with the emitter). The emitter and the found indirect receiver are considered to be associated with a signal path that passes through the tissue. Block S142 then includes defining the receiver considered immediately prior to the indirect receiver, along with the emitter, as a tangential emitter-receiver pair. The tangential emitter-receiver pair is thus a critical emitter-receiver pair that is immediately between one direct emitter-receiver pair and one indirect emitter-receiver pair. This process is preferably repeated for each emitter of the transducer array, such that the set of tangential emitter-receiver pairs describes, for each emitter of the transducer, a vector that is tangent to the tissue (or at least as close as possible to being tangent to the tissue, given the resolution offered by the transducer array). These tangential vectors (i.e., bounding vectors) preferably collectively define the tissue boundary, as shown in FIG. 4B.

In other variations, Blocks S140 and S142 can comprise iteratively cycling through the emitters and/or the receivers of the transducer array in any suitable manner to determine the set of tangential emitter-receiver pairs. Additionally, in some configurations of the transducer array, multiple tangential emitter-receiver pairs can share a common emitter or a common receiver. Furthermore, Blocks S140 and S142 can be adapted to further define tangential emitter-receiver pairs for concave tissue boundaries, based upon comparisons in power ratio and/or time-of-flight data between the baseline and the reconstruction datasets, or any other suitable comparison of any other suitable metric.

As shown in FIG. 1, the method 100 can further comprise Block S150, which recites determining a set of interior pixels of the reconstruction dataset, characterized by a set of pixel locations that are within the tissue boundary. Block S150 functions to determine whether a given pixel of the reconstruction dataset (i.e., on a reconstruction grid) lies inside or outside of the volume of tissue (e.g., on an "inner" or "outer" side of the tissue boundary). Whether a particular side of the tissue boundary is the inner or outer side depends on the checking direction in which the indirect receivers are identified in block S142. For example, in a first variation shown in FIG. 4A, block S142 identifies tangential emitter-receiver pairs by checking progressively distant receivers in a counter-clockwise direction. Therefore, the inner side of the tissue boundary is on the left side of the tangential vector originating from the emitter and directed toward the receiver of every tangential emitter-receiver pair. In a second variation, block S142 identifies tangential emitter-receiver pairs by checking progressively distant receivers in a clockwise direction. Therefore, the inner side of the tissue boundary is on the right side of the tangential vector originating from the emitter and directed toward the receiver of every tangential emitter-receiver pair in the second variation.

Figure 5:
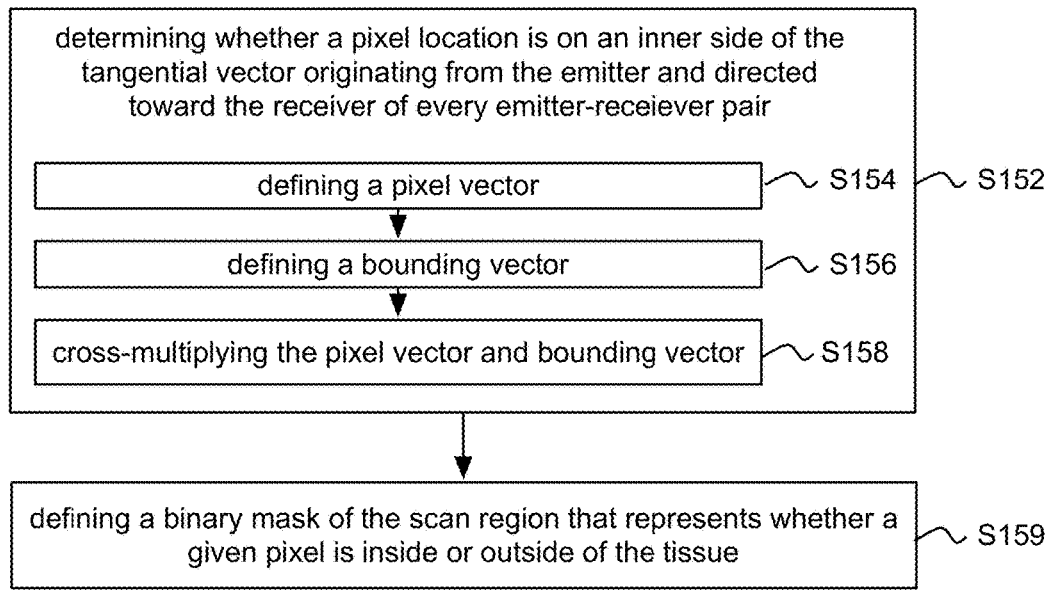
FIG. 5 is a flowchart depicting an embodiment of a portion of a method for imaging a volume of tissue.
Figure 6:
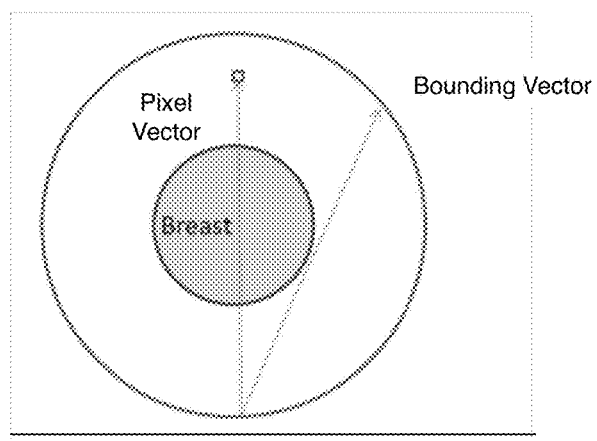
FIG. 6 is a schematic of an embodiment of portion of a method for imaging a volume of tissue.

As shown in FIG. 5, Block S150 preferably includes determining whether a pixel location of the reconstruction dataset is on an inner side of a tangential vector originating from the emitter and directed toward the receiver of every emitter-receiver pair S152. In particular, as shown in FIGS. 5 and 6, for a given pixel location, Block S152 preferably includes defining a pixel vector originating from an emitter and directed toward the pixel location S154, defining a bounding vector originating from the emitter and directed toward the receiver of the tangential emitter-receiver pair S156, and cross-multiplying the pixel vector and the bounding vector to determine whether the pixel corresponding to the pixel location lies to the left or right of the tangential vector S158. For each pixel/pixel location, Blocks S154, S156, and S158 are preferably repeated for every bounding vector. In other words, for every pixel, the method 100 preferably includes performing the cross-multiplication procedure with every bounding vector defined by the set of tangential emitter-receiver pairs. The cross-multiplication procedure can be performed sequentially with every bounding vector for a given pixel, or can be performed in any suitable order. Once a pixel is determined to be on the outer side of any bounding vector (and thus, the outer side of the tissue boundary), there is no need to continue performing Block S152 for additional bounding vectors for that pixel, because the pixel is already determined to be outside of the tissue boundary (e.g., based upon determining the existence of a critical pixel vector that places the pixel outside of the tissue boundary). Furthermore, Block S152 is preferably repeated for every pixel location under consideration for image reconstruction. As shown in FIG. 5, block S150 can further include defining a binary mask of each imaging plane, distinguishing every pixel on the inside of the tissue boundary from those on the outside of the tissue boundary (i.e., distinguishing the set of interior pixels), wherein the binary mask represents whether a given pixel is inside or outside of the tissue boundary in block S159.

In other variations, Block S140 can additionally or alternatively comprise defining the tissue boundary from a set of tangent points defined by the set of tangential emitter-receiver pairs, and defining global locations of the set of tangent points in order to determine whether a pixel location is within the tissue boundary in Step S150. In an example of these variations, a curve can be fitted to the global coordinates of the set of tangent points, and a pixel location can be determined to be within the tissue boundary if the coordinates of the pixel location are within every point along the curve fitted through the tangent points. Blocks S140 and S150 can, however, comprise any other suitable method of determining the tissue boundary and determining whether a pixel location is within the tissue boundary.

As shown in FIG. 1, the method 100 can also further include Block S160, which recites reconstructing pixels of the set of interior pixels, thereby transforming the baseline and the reconstruction datasets into an image rendering of the volume of tissue, characterized by selective reconstruction of the set of interior pixels. In particular, the reconstruction process of Block S160 is preferably limited to those pixels determined to be inside the tissue (i.e., the set of interior pixels), as determined by the binary mask generated in Block S159. The reconstruction is preferably based upon one or more of acoustic attenuation, acoustic reflection, acoustic speed, and/or any suitable acoustic parameter such as elasticity. Block S160 can include reconstruction methods, such as those described in U.S. patent application Ser. No. 13/566,778, entitled "Method and System for Multi-Grid Tomographic Inversion Tissue Imaging" and filed on 3 Aug. 2012, but can additionally and/or alternatively include any other suitable tomographic or reconstruction process(es). The method 100 preferably includes reconstructing a series of two-dimensional, cross-sectional images of the volume of tissue (e.g., by repeating at least a portion of blocks S110 through S160 for multiple cross-sectional slices of the tissue), and can alternatively include reconstructing a three-dimensional image rendering of the volume of tissue upon aggregation of all sets of interior pixels from multiple imaging planes.

2. System

Figure 8A:
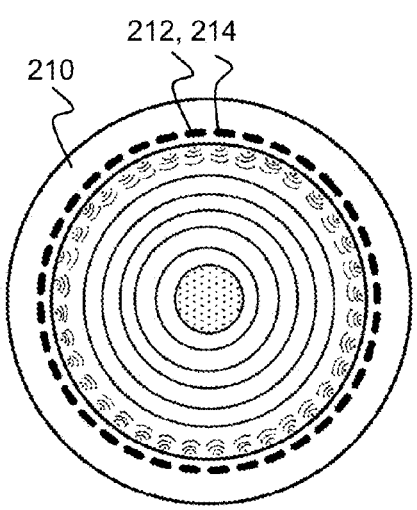
Figure 8B:
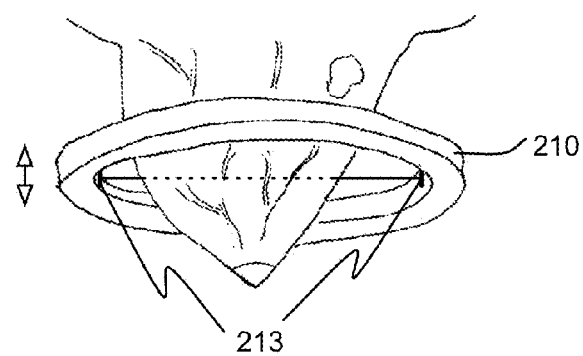

As shown in FIGS. 7, 8A, and 8B, an embodiment of a system 200 for imaging a scan region configured to include a volume of tissue surrounded by a medium includes: a transducer array 210 configured to surround the scan region, comprising a plurality of signal emitter-receiver pairs 213 each corresponding to a signal path intersecting at least one of the fluid medium and the tissue; and a processor 230 configured to determine the tissue boundary and generate an image rendering of the tissue based upon a baseline dataset and a reconstruction dataset gathered by the emitter-receiver pairs 213. The processes performed by the processor 230 can include one or more actions described in embodiments, variations, and examples of Blocks of the method 100 above. The system 200 can further include a display 240 on which the generated image rendering of the tissue can be displayed, such as to a medical practitioner and/or the patient.

The system 200 is preferably used to image a volume of tissue, such as breast tissue, for screening and/or diagnosis of cancer within the volume of tissue. In other applications, the system 200 can be used to characterize regions of interest in the tissue (e.g., to characterize suspicious masses as a tumor, a fibroadenoma, a cyst, another benign mass, or any suitable classification) or for monitoring status of the tissue such as throughout a cancer treatment. However, the system 200 can be used in any suitable application for imaging any suitable kind of tissue with ultrasound tomography.

The system 200 for imaging a volume of tissue with tissue boundary detection can provide a rapid, easy-to-use, ultrasound imaging modality that effectively identifies a tissue boundary of the scanned volume of tissue in multiple imaging planes, and enables differentiation between an image pixel location within the volume of tissue and an image pixel location outside of the volume of tissue. Such a differentiation can also be described as defining a binary "mask" which represents whether a given pixel is inside or outside of the volume of tissue. For example, the mask preferably enables faster image rendering times, and therefore shorter scans and patient exams without sacrificing image quality, since only pixels known to be within the tissue boundary are required to be reconstructed to create an image rendering of the tissue.

As shown in FIG. 8A, the transducer array 210 preferably comprises an ultrasound emitter array 212 and an ultrasound receiver array 214. The emitters of the ultrasound emitter array 212 and receivers of the ultrasound receiver array 214 can be piezoelectric or any suitable kind of ultrasound components (e.g., capacitive micromachined ultrasonic transducer elements). The ultrasound emitter array 212 functions to irradiate the scan region with acoustic waveforms from multiple locations distributed about the volume of tissue. The ultrasound receiver array 214 functions to receive the acoustic waveforms, which interact with the medium surrounding the volume of tissue and/or the volume of tissue. The emitters and receivers of the arrays 212, 214 preferably form a plurality of signal emitter-receiver pairs 213, each corresponding to a signal path intersecting at least one of the medium and the volume of tissue. The number of emitters in the transducer array 210 can be equal to the number of receivers in the transducer array 210, or the number of emitters in the transducer array 210 can alternatively be unequal to the number of receivers in the transducer array 210. Furthermore, each receiver can be mapped to every other emitter in the transducer array 210, or to only a subset of the emitters in the transducer array 210.

As shown in FIGS. 8A and 8B, the transducer array 210 is substantially ellipsoidal, substantially elliptical, or substantially circular in configuration, and preferably includes at least two hundred and fifty six evenly distributed ultrasound elements that each emits a fan beam of ultrasound signals toward the scan region, and receives ultrasound signals from other emitters. In alternative variations, the transducer array can be in any other suitable geometric configuration, comprise any other number of elements, and comprise elements that emit ultrasound signals defined by any other suitable signal profile(s). In one example of the system 200, the transducer array 210 includes 2048 evenly distributed ultrasound elements in a circular geometric configuration, in order to surround a volume of breast tissue.

As shown in FIG. 7, the transducer array 210 can be paired with a patient table having an aperture, such that a patient lying prone stomach-side down on the patient table can pass her breast through the aperture. In embodiments of the system 200 wherein the transducer array 210 is paired with a patient table, the patient table is preferably set up with a water bath, positioned beneath the patient table aperture, which receives the breast tissue and houses the ring transducer array 210 of the system 200. The transducer array 210, while surrounding the breast tissue, moves sequentially to a series of points along a vertical path (in the orientation shown in FIG. 7) in an anterior-posterior direction, scanning a two-dimensional cross-sectional image (e.g., coronal image) of the breast at each point, such that the received data can be used to generate a stack or series of two-dimensional images over the entire volume of tissue (and/or a three-dimensional volumetric image of the tissue). The water bath, which can alternatively be a bath of any suitable medium, preferably functions as an acoustic coupling medium between the transducer array 210 and the volume of tissue, and to suspend the breast tissue (thereby reducing gravitational distortion of the tissue). The transducer array 210 is preferably configured to perform an initial baseline scan of the scan region without the volume of tissue present in the medium, in order to generate a baseline dataset, and is preferably further configured to perform an imaging scan of the scan region with the volume of tissue present in the medium, in order to generate a reconstruction dataset.

Also shown in FIG. 7, the system 200 can also include a controller 220 that functions to control the actions of the transducer array 210. The controller 220 preferably controls the acoustic signals transmitted from the ultrasound emitter array 212 (e.g., frequency of waveforms, frequency of activation of the ultrasound emitters, signal strength) and/or the physical movements of the transducer array 210 relative to the volume of tissue. In particular, the controller 220 preferably controls motion of the transducer array 210, including dictating spacing between the scanning points at which the scanning occurs and/or the rate of travel between the scanning points. Furthermore, in one variation, the transducer array 210 can include one or more instances of a single physical transducer element that includes a set of ultrasound emitters and detectors, and the controller 220 can operate a switch or other controlling feature to selectively operate in either the transmitting or receiving/detecting mode.

The processor 230 functions to determine a tissue boundary characterizing the volume of tissue, and to generate an image rendering of the volume of tissue based upon a baseline dataset and a reconstruction dataset gathered by the emitter-receiver pairs of the transducer array 210. In particular, the processor 230 is preferably configured to receive a baseline dataset gathered by the emitter-receiver pairs 213 of the ultrasound emitter array 212 and the ultrasound receiver array 214, that is representative of a first set of signals interacting with a medium without the volume of tissue present in the medium. The processor 230 is also further configured to receive a reconstruction dataset gathered by the emitter-receiver pairs 213 of the ultrasound emitter array 212 and the ultrasound receiver array 214, that is representative of a second set of signals interacting with the fluid medium and tissue in the fluid medium. The processor 230 preferably utilizes the baseline and the reconstruction datasets to determine a set of tangential emitter-receiver pairs, each defining a bounding vector comprising a tangent point along the tissue boundary, and to generate an image rendering of the scan region based upon selective reconstruction of pixels within the tissue boundary.

Figure 9:
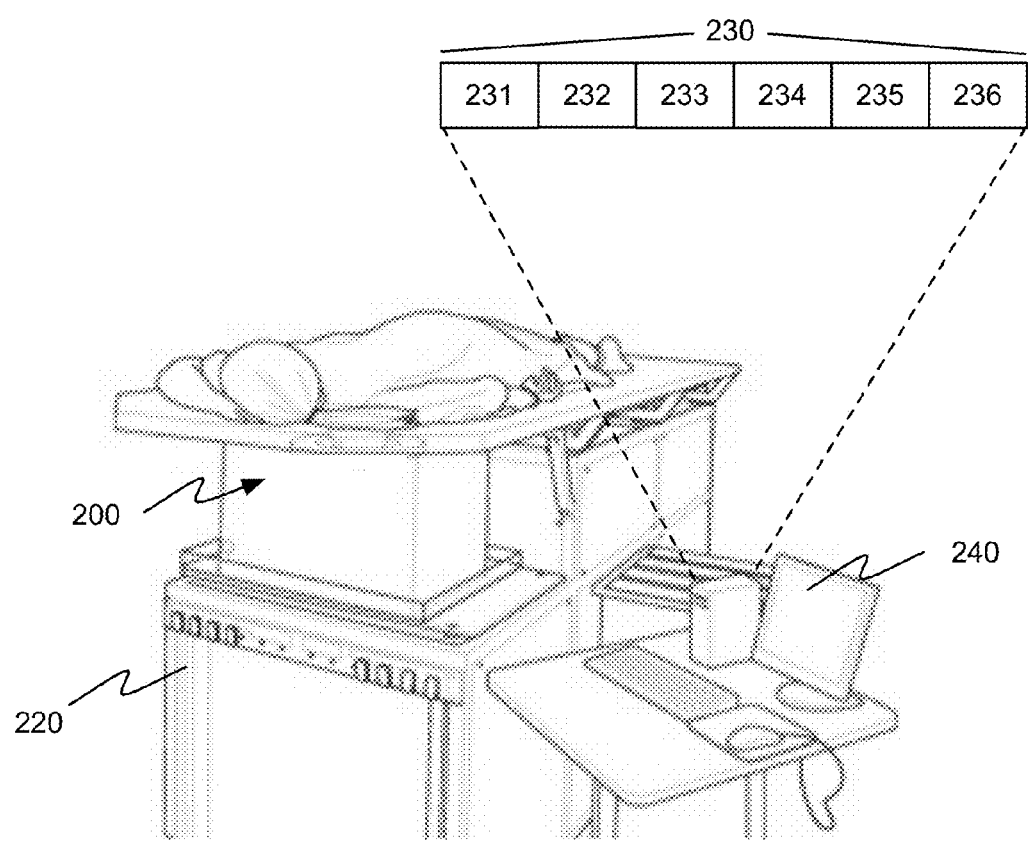
FIG. 9 is a schematic of an embodiment of a system for imaging a volume of tissue.

In one embodiment of the system 200, as shown in FIG. 9, the processor 230 preferably determines a tissue boundary within each of one or more cross-sectional slices of the volume of tissue, and generates an image rendering based upon selective reconstruction of pixels within the tissue boundaries, as described with reference to the method and variations thereof described above. As such, the processor 230 can comprise a first module 231 configured to receive a baseline dataset and a reconstruction dataset from the ultrasound emitter array and the ultrasound receiver array (e.g., from emitter-receiver pairs of the ultrasound transducer); a second module 232 configured to generate a set of similarity metrics (e.g., power ratio and time-of-flight similarity metrics), each similarity metric comparing a first metric of the baseline dataset associated with an emitter-receiver pair with a second metric of the reconstruction dataset associated with the emitter-receiver pair; a third module 233 configured to determine a set of direct emitter-receiver pairs, each defining a direct trajectory that does not pass through the volume of tissue; and a fourth module 234 configured to determine a set of tangential emitter-receiver pairs from the set of direct emitter-receiver pairs, each tangential emitter-receiver pair defining a bounding vector comprising a tangent point along the tissue boundary. The processor 230 can additionally comprise a fifth module 235 configured to determine a set of interior pixels, of the reconstruction dataset, characterized by a set of set of pixel locations that are within the tissue boundary; and a sixth module 236 configured to selectively reconstruct pixels of the set of interior pixels, thereby transforming the baseline and the reconstruction datasets into an image rendering of the volume of tissue.

The system 200 can, however, comprise any other suitable elements for generating and receiving baseline and reconstruction datasets, controlling acquisition and generation of the datasets, and processing the datasets in order to determine tissue boundaries and render images by selectively reconstructing pixels within the tissue boundaries.

Variations of the preferred system 200 and method 100 include any combination or permutation of the described components and processes. Furthermore, various processes of the preferred method can be embodied and/or implemented at least in part as a machine configured to receive a computer-readable medium storing computer-readable instructions. The instructions are preferably executed by computer-executable components preferably integrated with a suitable ultrasound scanning system and one or more portions of the controller 220 and/or processor 230. The computer-readable medium can be stored on any suitable computer readable media such as RAMs, ROMs, flash memory, EEPROMs, optical devices (CD or DVD), hard drives, floppy drives, or any suitable device. The computer-executable component is preferably a general or application specific processor, but any suitable dedicated hardware device or hardware/firmware combination device can additionally or alternatively execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A method for imaging a volume of tissue and defining a boundary of the volume of tissue using an ultrasound transducer array comprising a set of emitter-receiver pairs, the method comprising:

acquiring a baseline dataset and a reconstruction dataset with the ultrasound transducer array, wherein the baseline dataset is representative of a first set of signals interacting with a medium without the volume of tissue present in the medium and the reconstruction dataset is representative of a second set of signals interacting with the medium and the volume of tissue present in the medium;

receiving the baseline dataset from the set of emitter-receiver pairs;

receiving the reconstruction dataset from the set of emitter-receiver pairs;

generating a set of similarity metrics, each similarity metric comparing a first metric of the baseline dataset, associated with an emitter-receiver pair from the set of emitter-receiver pairs, with a second metric of the reconstruction dataset, associated with the emitter-receiver pair;

based upon the set of similarity metrics, determining a set of direct emitter-receiver pairs, wherein each direct emitter-receiver pair in the set of direct emitter-receiver pairs defines a direct trajectory that does not pass through the volume of tissue;

from the set of direct emitter-receiver pairs, determining a set of tangential emitter-receiver pairs, wherein each tangential emitter-receiver pair in the set of tangential emitter-receiver pairs defines a bounding vector comprising a tangent point along the boundary; and transforming the reconstruction dataset into an image rendering, based upon reconstruction of a set of interior pixels of the reconstruction dataset, that are within the boundary.

2. The method of claim 1, wherein receiving the baseline dataset and the reconstruction dataset comprise receiving the baseline dataset and the reconstruction dataset at an ultrasound emitter array, configured to surround a scan region for the volume of tissue and emit acoustic signals toward the scan region, and an ultrasound receiver array, configured to surround the scan region and receive acoustic signals from the scan region.

3. The method of claim 1, wherein generating the set of similarity metrics, comprises:

for each emitter-receiver pair of the set of emitter-receiver pairs, generating a power ratio similarity metric comparing a first power ratio of the baseline dataset with a second power ratio of the reconstruction dataset, wherein the first and the second power ratio are associated with the emitter-receiver pair, and for each emitter-receiver pair of the set of emitter-receiver pairs, generating a time-of-flight similarity metric comparing a first time-of-flight of the baseline dataset with a second time-of-flight of the reconstruction dataset, wherein the first and the second time-of-flight are associated with the emitter-receiver pair.

4. The method of claim 3, wherein determining the set of direct emitter-receiver pairs comprises: for each emitter-receiver pair in the set of direct emitter-receiver pairs, adding an emitter-receiver pair to the set of direct emitter-receiver pairs if the power-ratio similarity metric of the emitter-receiver pair satisfies a first threshold and the time-of-flight similarity metric for the emitter-receiver pair satisfies a second threshold.

5. The method of claim 1, wherein determining the set of tangential emitter-receiver pairs comprises:

forming a binary logic matrix that identifies the set of direct emitter-receiver pairs of the set of emitter-receiver pairs;

for each emitter in the ultrasound transducer array, checking progressively distant receivers with the emitter, against the binary logic matrix, until a critical emitter-receiver pair is found, wherein the critical emitter-receiver pair is between one direct-emitter receiver pair of the set of direct emitter-receiver pairs and an indirect emitter-receiver pair; and adding the critical emitter-receiver pair to the set of tangential emitter-receiver pairs.

6. The method of claim 1, further comprising fitting a curve through a set of tangent points to the boundary, defined by the set of tangential emitter-receiver pairs.

7. The method of claim 1, further comprising determining the set of interior pixels of the reconstruction dataset that are within the tissue boundary.

8. The method of claim 7, wherein determining the set of interior pixels comprises:

for a pixel of the reconstruction dataset, forming a pixel vector from each emitter of the set of tangential emitter-receiver pairs toward the pixel, thereby forming a set of pixel vectors for the pixel, generating a set of comparisons between the set of pixel vectors and the set of bounding vectors, and adding the pixel to the set of interior pixels if the pixel is within every bounding vector of the set of bounding vectors, as determined from the set of comparisons.

9. The method of claim 8, wherein generating the set of comparisons comprises cross-multiplying a pixel vector and a bounding vector that share an emitter of the set of tangential emitter-receiver pairs.

10. The method of claim 7, wherein reconstructing pixels of the set of interior pixels comprises reconstructing pixels based upon at least one of acoustic attenuation, acoustic reflection, and acoustic speed.

11. A method for imaging a volume of tissue and defining a boundary of the volume of tissue using an ultrasound transducer array comprising a set of emitter-receiver pairs, the method comprising:

acquiring a baseline dataset and a reconstruction dataset with the ultrasound transducer array, wherein the baseline dataset is representative of a first set of signals interacting with a medium without the volume of tissue present in the medium and the reconstruction dataset is representative of a second set of signals interacting with the medium and the volume of tissue present in the medium;

receiving the baseline dataset from the set of emitter-receiver pairs;

receiving the reconstruction dataset from the set of emitter-receiver pairs;

from the baseline and the reconstruction datasets, determining a set of tangential emitter-receiver pairs, wherein each tangential emitter-receiver pair in the set of tangential emitter-receiver pairs defines a bounding vector comprising a tangent point along the boundary, thereby defining a set of bounding vectors; and for each pixel of the reconstruction dataset, determining if the pixel is within the boundary, wherein determining comprises:

forming a pixel vector from each emitter of the set of tangential emitter-receiver pairs toward the pixel, thereby forming a set of pixel vectors for the pixel, generating a set of comparisons between the set of pixel vectors and the set of bounding vectors, adding the pixel to the set of interior pixels if the pixel is within every bounding vector of the set of bounding vectors, as determined from the set of comparisons; and reconstructing pixels determined to be within the boundary, thereby transforming the baseline and the reconstruction datasets into an image rendering of the volume of tissue.

12. The method of claim 11, wherein receiving the baseline dataset and the reconstruction dataset comprise receiving the baseline dataset and the reconstruction dataset at an ultrasound emitter array, configured to surround a scan region for the volume of tissue and emit acoustic signals toward the scan region, and an ultrasound receiver array, configured to surround the scan region and receive acoustic signals from the scan region.

13. The method of claim 11, wherein determining the set of tangential emitter-receiver pairs from the baseline and the reconstruction datasets comprises:

generating a set of similarity metrics, each similarity metric comparing a first metric of the baseline dataset, associated with an emitter-receiver pair from the set of emitter-receiver pairs, with a second metric of the reconstruction dataset, associated with the emitter-receiver pair, based upon the set of similarity metrics, determining a set of direct emitter-receiver pairs, wherein each direct emitter-receiver pair in the set of direct emitter-receiver pairs defines a direct trajectory that does not pass through the volume of tissue, forming a binary logic matrix that identifies the set of direct emitter-receiver pairs of the set of emitter-receiver pairs, for each emitter in the ultrasound transducer array, checking progressively distant receivers with the emitter, against the binary logic matrix, until a critical emitter-receiver pair is found, wherein the critical emitter-receiver pair is between one direct-emitter receiver pair of the set of direct emitter-receiver pairs and an indirect emitter-receiver pair, and adding the critical emitter-receiver pair to the set of tangential emitter-receiver pairs.

14. The method of claim 11, wherein generating the set of comparisons comprises cross-multiplying a pixel vector and a bounding vector, wherein the pixel vector and the bounding vector share an emitter of the set of tangential emitter-receiver pairs.

15. The method of claim 11, wherein reconstructing pixels determined to be within the boundary comprises reconstructing pixels based upon at least one of acoustic attenuation, acoustic reflection, and acoustic speed.

16. The method of claim 11, further comprising selectively reconstructing pixels within tissue boundaries of multiple imaging planes, thereby transforming the baseline and the reconstruction datasets into a three-dimensional rendering of the volume of tissue.

* * * * *

UNITED STATES PATENT AND TRADEMARK OFFICE
CERTIFICATE OF CORRECTION

| | |
|---|---|
| PATENT NO. | : 9,763,641 B2 |
| APPLICATION NO. | : 14/015459 |
| DATED | : September 19, 2017 |
| INVENTOR(S) | : Erik West, Olivier Roy and Steven Schmidt |

Page 1 of 1

It is certified that error appears in the above-identified patent and that said Letters Patent is hereby corrected as shown below:

In the Specification

In Column 1, Line 11, insert following header and paragraph:
--STATEMENT AS TO FEDERALLY SPONSORED RESEARCH
This invention was made with Government support under Grant R44CA165320 awarded by the National Institutes of Health (NIH) through the National Cancer Institute. The Government has certain rights in the invention.--

Signed and Sealed this
Thirtieth Day of July, 2024

Katherine Kelly Vidal
*Director of the United States Patent and Trademark Office*